(12) United States Patent
Meythaler et al.

(10) Patent No.: US 7,014,624 B2
(45) Date of Patent: Mar. 21, 2006

(54) DIRECT CENTRAL NERVOUS SYSTEM CATHETER AND TEMPERATURE CONTROL SYSTEM

(75) Inventors: Jay M. Meythaler, Birmingham, AL (US); Jean D. Peduzzi-Nelson, Chelsea, AL (US); Landon C. Miller, Tuscaloosa, AL (US)

(73) Assignee: The UAB Research Foundation, Birmingham, AL (US)

( * ) Notice: Subject to any disclaimer, the term of this patent is extended or adjusted under 35 U.S.C. 154(b) by 269 days.

(21) Appl. No.: 10/443,210

(22) Filed: May 22, 2003

(65) Prior Publication Data
US 2004/0024358 A1    Feb. 5, 2004

Related U.S. Application Data

(63) Continuation-in-part of application No. 09/914,801, filed as application No. PCT/US00/05740 on Mar. 3, 2000, now Pat. No. 6,682,508.

(60) Provisional application No. 60/148,055, filed on Aug. 10, 1999, provisional application No. 60/122,642, filed on Mar. 3, 1999.

(51) Int. Cl.
| A61F 7/12 | (2006.01) |
| H05B 3/00 | (2006.01) |
| A61M 31/00 | (2006.01) |
| A61M 25/00 | (2006.01) |
| A61M 25/18 | (2006.01) |

(52) U.S. Cl. .................. 604/113; 604/66; 604/284; 604/537; 600/485; 600/561; 607/62

(58) Field of Classification Search ............... 604/43, 604/48, 505, 508, 65–67, 93.01, 113–114, 604/151, 246–249, 256, 257, 264, 268, 523, 604/533, 534–535, 284, 890.1; 607/62, 96–99; 137/340; 606/27–31; 600/549, 561, 573, 600/581, 485
See application file for complete search history.

(56) References Cited

U.S. PATENT DOCUMENTS

| 4,613,324 A | 9/1986 | Ghajar ................. 604/49 |
| 4,621,647 A * | 11/1986 | Loveland ............. 600/561 |

(Continued)

Primary Examiner—Nicholas D. Lucchesi
Assistant Examiner—Catherine S. Williams
(74) Attorney, Agent, or Firm—Gifford, Krass, Groh, Sprinkle, Anderson & Citkowski, P.C.

(57) ABSTRACT

A central nervous system (CNS) catheter assembly adapted for use as a ventriculostomy catheter and a spinal catheter includes a catheter body defining at least one lumen therethrough having a drug delivery branch and a monitoring/sensing branch. The drug delivery branch and the monitoring/sensing second branch are in fluid communication with the lumen. Openings are disposed in fluid communication with the lumen and being located at proximal ends of the drug delivery branch and the monitoring/sensing branch. Another opening is disposed at a distal end of the main body. The assembly further includes a component such as an intracranial pressure/osmotic pressure monitoring system, a fluid drainage system, an attachable introduction aid, a patient surface attachment aid, a micromanipulator and a comprehensive intracranial pressure evaluation and relief system. The assembly optionally includes a filter assembly containing a proton exchange membrane.

30 Claims, 10 Drawing Sheets

U.S. PATENT DOCUMENTS

| | | | |
|---|---|---|---|
| 4,655,745 A | 4/1987 | Corbett | 604/49 |
| 4,723,556 A | 2/1988 | Sussman | 128/748 |
| 4,784,638 A | 11/1988 | Ghajar et al. | 604/49 |
| 4,904,237 A | 2/1990 | Janese | 604/28 |
| 4,950,232 A | 8/1990 | Ruzicka et al. | 604/43 |
| 5,360,397 A | 11/1994 | Pinchuk | 604/27 |
| 5,364,377 A | 11/1994 | O'Neil | 156/294 |
| 5,474,547 A | 12/1995 | Aebisher et al. | 604/891.1 |
| 5,531,673 A | 7/1996 | Helenowski | 604/9 |
| 5,569,267 A | 10/1996 | Howard, III et al. | 606/130 |
| 5,772,625 A | 6/1998 | Krueger et al. | 604/9 |
| 5,832,932 A | 11/1998 | Elsberry et al. | 128/898 |
| 5,846,220 A | 12/1998 | Elsberry | 604/49 |
| 5,897,528 A | 4/1999 | Schultz | 604/49 |
| 5,957,912 A | 9/1999 | Heitzmann | 604/533 |
| 5,964,705 A | 10/1999 | Truwit et al. | 600/423 |
| 6,026,316 A | 2/2000 | Kucharczyk et al. | 600/420 |
| 6,061,587 A | 5/2000 | Kucharczyk et al. | 600/411 |

\* cited by examiner

DIRECT CENTRAL NERVOUS SYSTEM CATHETER AND TEMPERATURE CONTROL SYSTEM

RELATED APPLICATIONS

This application is a continuation-in-part of U.S. patent application Ser. No. 09/914,801 filed Dec. 3, 2001, now U.S. Pat. No. 6,682,503 which is a national phase of PCT Application No. PCT/US00/05740 filed Mar. 3, 2000, which claims priority of U.S. Provisional Application 60/122,642 filed Mar. 3, 1999 and U.S. Provisional Application 60/148,055 filed Aug. 10, 1999.

FIELD OF THE INVENTION

The subject invention relates to a catheter assembly and, more specifically, to a direct central nervous system catheter assembly suitable for use for: the simultaneous measurement of intracranial pressure, draining of cerebrospinal fluid (CSF), delivery of therapeutic agents and/or drug(s) directly into the cerebrospinal fluid, and a temperature control system which can be coupled to the direct central nervous system catheter to prevent or reduce damage to the central nervous system.

BACKGROUND OF THE INVENTION

By way of background, ventriculostomy catheters are commonly used to facilitate the drainage of cerebrospinal fluid (CSF) to reduce intracerebral pressure and can also be connected to pressure transducers for the monitoring of intracranial pressure (ICP). The increased use of ventriculostomy catheters can be directly associated with the publication of Guidelines to the Management of Severe Head Injury (Bullock et al. (1995) Guidelines for the Management of Severe Head Injury. San Francisco: Brain Trauma Foundation, Inc.; Rosner et al. (1992) *J. Neurosurgery* 76:399A; Rosner et al. (1990) *J. Trauma* 30:933–41; Rosner (1987) "Cerebral perfusion pressure: The link between intracranial pressure and systemic circulation". In Wood (ed.): Cerebral Flood Flow: Physiologic and Clinical Aspects. McGraw Hill, New York, N.Y., pp. 425–88, 1987). These Guidelines recommend the use of either a pressure bolt against the cerebral membranes or that a ventriculostomy be performed to directly measure ICP in all patients with a head injury and a glasgow coma score (GCS) of less than 10. Additionally, ventriculostomies are often utilized because of the added feature of allowing direct access to the CSF at the level of the brain. This is of particular importance as these catheters allow direct access to the CSF, which allows for direct withdrawal of CSF to control increased intracranial pressure, monitor drug levels or metabolites in the CSF (Kossman et al. (1996) *J. Antimicrob. Chemother.* 37(1):161–7), or to remove toxic substances from the CSF flow (Kristof et al. (1998) *J. Neurol. Neurosurg. Psychiatry.* 64(3):379–81).

Current ventriculostomy catheters are generally "open systems" of the single lumen-type, and as stated above, are typically linked to pressure transducers to give measurements of ICP, and are used to facilitate the drainage of CSF to reduce intracerebral pressure by disconnecting the pressure monitor and extracting CSF fluid, and then reconnecting the pressure monitor. This creates the potential for the introduction of infectious agents which can cause infections such as ventriculitis or meningitis. As such, one of the most significant concerns of intracranial pressure monitoring is the potential introduction of pathogens into the CNS resulting in ventriculitis, meningitis and cerebral abscesses (Rossi et al. (1998) *Acta Neurochir. Suppl.* 71:91–3; Khan et al. (1998) *Acta Neurochir. Suppl.* 71:50–2; Guyot et al. (1998) *Acta Neurochir. Suppl.* 71:47–9; Holloway et al. (1996) *J. Neurosurg.* 85(3):419–24). The current ventriculostomy catheters are not designed, nor was it ever envisioned, that they would be used for drug delivery directly into the CSF. Furthermore, they are not generally approved for this use although some instances have been reported where they have been used for the delivery of antibiotics into the CSF. However, use of current ventriculostomy catheters in this manner remains a "non-approved use."

Similar to the present day ventriculostomy catheters, spinal catheters having an external port have been utilized for many years for the sampling of CSF and for the delivery of medications to the CSF in and around the spinal cord. These medications include anesthetics and acute pain medications. In animal models of induced CNS injury it has been suggested that intrathecal or intraventricular delivery may be of use to attenuate the amount of injury (Buki et al. (1999) *J. Neurotrauma* 16(6):511–21).

While the current ventriculostomy catheters and spinal catheters have been utilized for the introduction of drugs or medications therethrough, the current types of these catheters are not specifically designed for the delivery of drugs therethrough and, hence, impart drawbacks, the most critical of which includes the opportunity for and the introduction of infectious agents directly into the cerebral spinal fluid causing, for example, ventriculitis and/or meningitis.

It is known that in order to prevent or reduce injury or damage to elements of the central nervous system, such as the brain or spinal cord, that artificial conditions can be induced in the central nervous system such as the induction of a coma to slow the metabolism of the brain to keep its tissues viable. One such method for accomplishing this end is disclosed in U.S. Pat. No. 5,149,321 to Klatz et al. in which chilled drug containing fluids are delivered to the brain through catheters inserted in blood vessels such as the carotid artery. However, the prior art does not teach a method for directly maintaining or controlling the temperature of the CSF to aid in the treatment of central nervous system injuries.

Temperature has been linked to the degree of injury in CNS trauma induced in animals (Clark et al. (1996) *J. Cereb. Blood Flow Metab.* 16(2):253–61; Whalen et al. (1997) *J. Neurotrauma* 14(8):561–72). In essence, if the temperature can be lowered there will be a reduction in the area and amount of neuronal damage (Dietrich (1992) *J. Neurotrauma* 9 Suppl. 2:S475–85; Dietrich et al. (1996) *Adv. Neurol.* 71:177–94, discussion 194–7; Palmer et al. (1993) *J Neurotrauma* 10(4):363–72). It has recently been theorized that a local reduction in the area of injury is required to reduce the amount and extent of induced injury to the brain while avoiding the complications associated with whole body cooling (Dietrich et al. (1996) *Adv. Neurol.* 71:177–94, discussion 194–7). It is likely that these same principles apply to spinal cord injury.

Accordingly, it would be both advantageous and desirable to have a catheter design which allows both direct access to the central nervous system (CNS) (e.g., the cerebral spinal fluid disposed about the brain and/or spinal cord) which would facilitate the measurement of ICP, the removal of CSF under aseptic circumstances, the aseptic introduction of therapeutic agents and/or drugs directly into the cerebral spinal fluid, and which can be combined with a temperature control system to control the temperature of the CSF to prevent or reduce damage to the central nervous system and to facilitate treatment of an individual in need of such treatment.

SUMMARY OF THE INVENTION

In accordance with the present invention, there is provided a direct central nervous system catheter which can be directly inserted into the ventricle space or spinal canal to provide access which enables the sampling of the CSF and/or monitoring of intracranial pressure while at the same time facilitating the aseptic delivery of therapeutic agents and/or drugs directly into the cerebrospinal fluid and the management of CSF temperature. The direct CNS catheter includes a catheter body defining at least one lumen and having a drug delivery branch, a monitoring/sensing branch, and optional branches if desired, each branch being connected in fluid communication with the lumen. Both the drug delivery branch and the monitoring branch have at least one proximally disposed opening which provides for the introduction and/or removal of fluid therefrom. The drug delivery branch of the catheter assembly includes a filter connected in fluid communication therewith to remove any pathogens from a therapeutic agent and/or drug(s) delivered to the cerebrospinal fluid through the branch. The catheter assembly can also include a one-way valve for the introduction of drugs, fluids or medications through the catheter assembly with no back-flow of the introduced materials. With this design, the catheter assembly limits the introduction of pathogens into the system and reduces the potential contact of the health care provider to bodily fluids. Finally, the catheter assembly reduces the risk of losing an introduced therapeutic agent due to back-flow. The drug delivery branch is disposed distally to a sampling branch which allows for the withdrawal of fluids. The monitoring branch allows for direct measurement of CSF pressure using monitoring or sensing equipment. This includes monitoring pressure waves of the cerebrospinal fluid through the end of the catheter placed in the ventricle or spinal canal of a brain. The catheter assembly can also include a control valve disposed in fluid communication with an optional branch which includes an in-line one-way valve that allows the direct sampling of the cerebrospinal fluid for either laboratory testing or to lower intracranial pressure in a sterile fashion. The monitoring branch is connected in fluid communication with the catheter body through a second control valve. The monitoring branch allows for pressure monitoring or sensing and the control valve allows for the measurement of intracranial pressure in a first position wherein an open fluid pathway is established between the portion of the catheter disposed in the ventricle or spinal canal and the monitoring branch and wherein fluid communication between the portion of the catheter in the ventricle or spinal canal and the fluid sampling branch is closed. The control valve is movable to a second position wherein fluid communication between the portion of the catheter inserted in the ventricle or spinal canal and the sampling branch is opened whereby fluid can be extracted from the patient. In the second portion, fluid communication between the pressure monitoring branch and the portion of the catheter disposed in the ventricle or spinal canal is closed.

Also in accordance with the present invention, there is provided a component selected from the following: an intracranial pressure/osmotic pressure monitoring system, a fluid drainage system, an attachable introduction aid, a patient surface attachment aid, a micromanipulator and a comprehensive intracranial pressure evaluation and relief system. Optionally, a membrane assembly is included containing a proton exchange membrane.

BRIEF DESCRIPTION OF THE DRAWINGS

The following detailed description is best understood with reference to the following drawings in which.

DETAILED DESCRIPTION OF THE INVENTION

Figure 1:
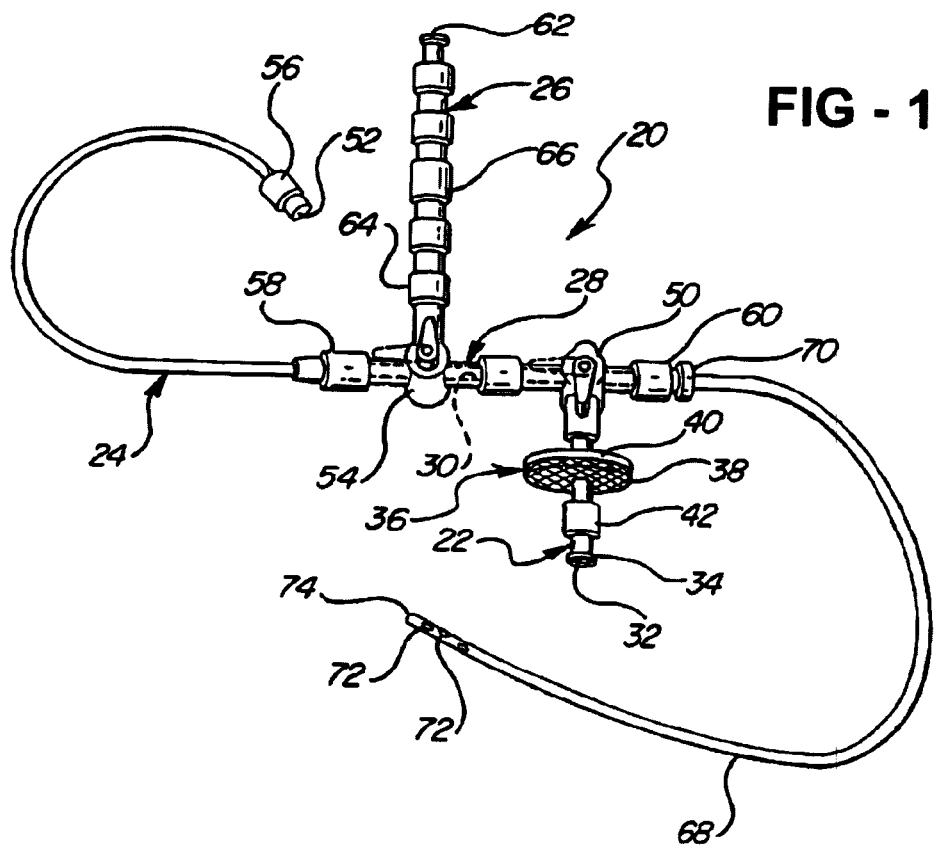
FIG. 1 is a perspective view of an embodiment of the catheter assembly of the present invention.

Referring to FIG. 1, a central nervous system (CNS) catheter assembly is generally shown at 20. The assembly 20 is to be inserted via an insertion device such as a wire disposed inside the catheter assembly 20 into either the spinal canal or ventricles of the brain in order to remove cerebrospinal fluid (CSF), monitor intracranial pressure (ICP), and/or deliver therapeutic agents and/or drugs intrathecally and/or intraventricularly, directly into the cerebrospinal fluid.

The CNS catheter assembly 20 includes branches 22, 24, 26 and a main body 28 which defines at least one lumen 30 therethrough. The branches 22, 24, 26 and main catheter body 28 are preferably tubular in shape.

The branch 22 includes a proximally disposed opening or port 32 which provides access to the lumen 30. The branch 22 is preferably designed for the introduction or delivery of drugs therethrough. The branch 22 can also include a connector or adapter 34 disposed directly adjacent to or about the proximal opening or port 32 which allows for the connection or attachment of a fluid delivery device, such as a syringe, to the branch 22 for delivery of a therapeutic agent and/or a drug therethrough. The connector 34 can be any suitable connector such as a modular-type connector, a quick-release or Luer-type connector, a cap having, for example, a reclosable diaphragm to allow repeated needle puncturing, or other screw down-type connectors, all of which are well known to those skilled in the art.

The branch 22 further includes a micro-filter assembly 36 which is disposed in-line and in fluid communication with the branch 22. The filter assembly 36 allows for the aseptic introduction of drugs into the cerebrospinal fluid of a patient without the potential for delivery of harmful microorganisms into the cerebrospinal fluid which can cause CNS infections including ventriculitis or meningitis. Preferably, the filter assembly 36 includes a membrane-type or micropore filter 38 disposed substantially perpendicular with respect to the lumen 30 and fluid flow path. That is, the filter 38 lies transversely across or substantially perpendicular to the lumen 30. The filter assembly 36 can also include a support 40 which provides support to the filter 38 during the delivery of the drug therethrough to enable the filter 38 to withstand pressures applied by the fluid delivery device. The filter 38 can include any suitable filter media which can include any suitable hydrophobic or hydrophilic material such as cellulose fiber, polysulfones, polyamides, polyolefins, polyesters, and fluoropolymers. This list of materials is not intended to be exhaustive and other suitable materials can be utilized without departing from the present invention.

Figure 2:
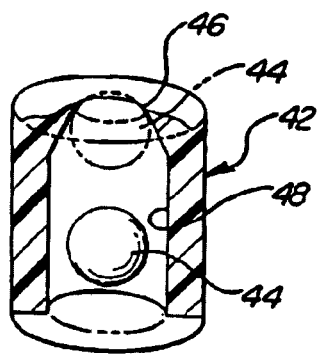
FIG. 2 is an enlarged perspective view of a valve assembly for the present invention.

The branch 22 can also include a one-way valve 42 disposed in between the filter assembly 36 and the connector 34 which prevents back-flow of fluid into the catheter assembly 20 and/or the ventricle space or spinal canal. Referring to FIG. 2, the valve 42 is preferably a one-way valve or other suitable type or design including a ball valve or any other type or design known to those skilled in the art which remains in a closed position to drug delivery (shown in phantom) wherein the ball 44 seals an opening 46, until the pressure exerted on the ball 44 by the drug delivery forces the ball 44 to move to an open position 44' wherein the ball 44 is clear of the opening 46 to allow the drug to flow into the filter assembly 36. The valve 42, as shown in FIG. 2, is activated by the back pressure from the CSF or any other cause. In this valve assembly, back pressure from the CSF or any other cause maintains a ball 44 disposed in a conduit 48 in a first position (shown in phantom) directly adjacent to and in contact with the opening 46 to prevent flow through the valve assembly 42. Then, upon the application of pressure from the delivery of a drug or the like through the valve assembly 42, the ball 44 would be displaced to a second position (as shown) away from the opening 46 whereby the flow path through the conduit 48 allows the movement of fluid, i.e., drugs, to pass through the valve assembly 42 and ultimately into the patient.

The branch 22 is disposed in fluid communication with the main body 28 and can include a multi-position control valve 50 disposed therebetween to, in a first position (shown in phantom), allow the introduction of a drug through the branch 22 while preventing any drug from flowing in the proximal direction, and, in a second position (as shown), allow for pressure monitoring and/or fluid extraction while closing the drug delivery pathway.

The branch 24 can be used as an ICP monitoring/sensing branch which includes a proximally disposed-opening or port 52 which can be attached to a pressure transducer in order to monitor ICP or other parameters and/or to allow the removal of CSF. The pressure monitoring branch 24 can also be connected to a multi-position control valve 54 disposed in fluid communication therewith. The control valve 54 is preferably a multi-position valve which prevents the flow of fluid distally away from the opening or port 52 and also maintains a constant pressure so that the pressure monitoring branch 24 of the catheter assembly 20 is not compromised by fluid flowing in the reverse direction. The valve 54 is movable between a first position (as shown) wherein the monitoring branch 24 is in fluid communication with the main body 28 and the portion of the catheter assembly 20 disposed in the ventricle or spinal canal to allow ICP monitoring and a second position (shown in phantom) wherein ICP monitoring through the monitoring branch 24 is interrupted or closed and fluid communication between the third/sampling branch 26 and the main body 28 and the portion of the catheter disposed in the ventricle or spinal canal is established. The valve assemblies 50, 54 can be any suitable valve known to those skilled in the art such as a standard ball-cock valve or stop-cock valve. The valves 50, 54 are preferably three-way valves having a first position, a second position, and a third position.

The branch 24 can also include a connector 56 similar to that of connector 34 described above disposed adjacent to the opening or port 52 to facilitate the use of the branch 24 with various devices including a pressure transducer and/or syringe and/or needle.

Additionally, at least one connector 58, similar in style to the connector 34 and preferably without the reclosable diaphragm, can be disposed in-line as shown in FIG. 1. A further optional connector 60 similar to the connector 34 but preferably without a diaphragm can be disposed in-line in the catheter body 28 as shown in FIG. 1.

The sampling branch 26 is disposed in fluid communication with the main body 28. The multi-position control valve 54 is disposed between the branch 26 and the main body 28. The sampling branch 26 includes an opening or port 62 disposed at its distal end. A connector 64 similar to those discussed above can also be disposed at the distal end of the branch 26. The sampling branch 26 can also include a one-way valve 66 disposed between the port 62 and the valve 54 similar to the valve 42 described above. The valve 66 is oriented in the opposite direction to the valve 42 to allow fluid withdrawal or extraction.

At the distal end of the catheter body 28, an intraventricular or spinal canal catheter portion 68 is affixed. The intraventricular or spinal canal catheter portion 68 is the portion of the catheter assembly 20 inserted into the ventricle space or the spinal canal. The intraventricular or spinal canal portion 68 can be permanently affixed to the catheter body 28 or it can be connected through a connector 70 to the connector 60 such as following placement of the intraventricular or spinal canal catheter portion 68 within a patient. The intraventricular or spinal canal catheter portion 68 can include at least one port 72 disposed substantially adjacent to an end or distal tip 74 of the main body 28 of the catheter assembly 20. The end 74 may or may not be closed. In a preferred embodiment, shown in FIG. 1, several ports 72 are helically disposed on the intraventricular or spinal canal catheter portion 68. Each port 72 can be formed by using a low power laser to ablate material to form the port 72. In operation, the end 74 of the catheter assembly 20 is inserted into either the intraventricular space or the spinal canal in order to place the port 72 in contact with the CSF. The end 74 can also include a diaphragm which can remain closed or, when pierced, will remain open. That is, the diaphragm is not self-sealing.

Figure 3:
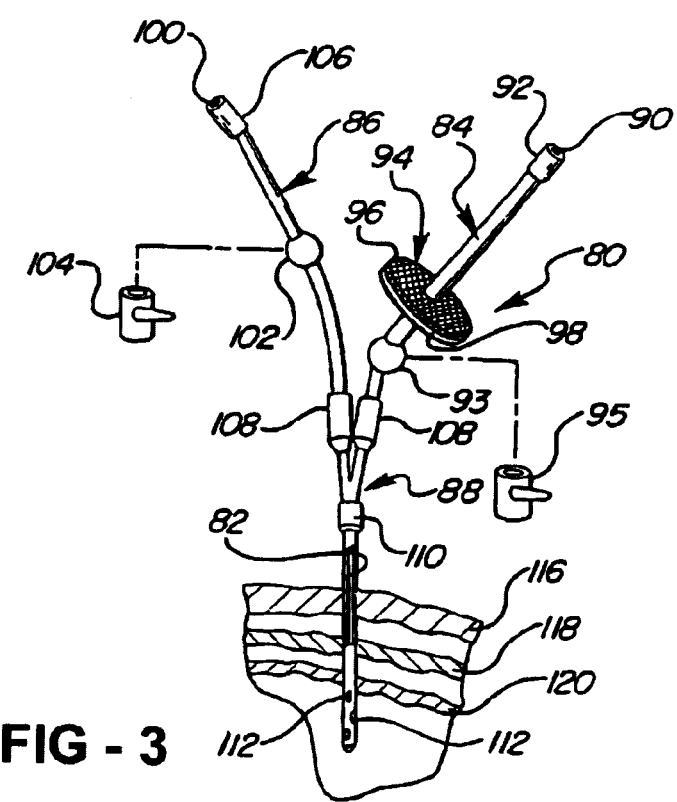
FIG. 3 is a schematic diagram illustrating an alternative embodiment of the CNS catheter of the present invention.

Referring to FIG. 3, an alternative embodiment of the central nervous system (CNS) catheter assembly is generally shown at 80. The assembly 80 is to be inserted into either the spinal canal or ventricles of the brain in order to remove cerebrospinal fluid (CSP) via an insertion device such as a wire disposed inside a lumen 82, to monitor intracranial pressure (ICP), and/or deliver drugs, such as intrathecally, directly into the cerebrospinal fluid.

The CNS catheter assembly 80 includes a pair of branches 84, 86 and a main body 88 which defines at least one lumen 82 therethrough. Both the branches 84, 86 and main body 88 are preferably oriented in an essentially "Y" shaped orientation.

Figure 4:
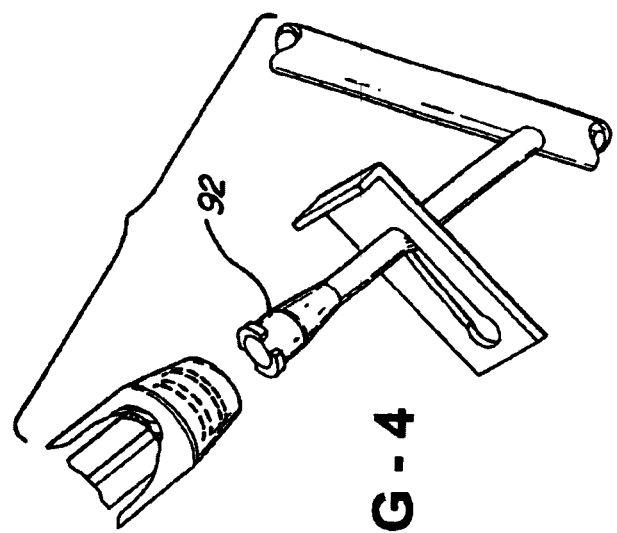
FIG. 4 is an enlarged view of a connector used in cooperation with the catheter assembly of the present invention.

The branch 84 includes a proximally disposed opening 90 which provides access to the lumen 82. The branch 84 is preferably designed for the introduction or delivery of drugs therethrough. The branch 84 can also include a connector or adapter 92 disposed directly adjacent to or about the proximal opening or port 90 which allows for the connection or attachment of a fluid delivery device, such as a syringe, to the branch 84 for delivery of a drug therethrough. The connector 92 can be any suitable connector such as a quick-release or Luer-type connector capable of attaching a syringe thereto, for example (see FIG. 4), a cap having a reclosable diaphragm to allow repeated needle puncturing, or other screw down-type connectors known to those skilled in the art. It may also be a one-way valve similar to the valve 42 described above.

The branch 84 can also include a valve assembly 93 which is preferably a one-way valve similar to those described above but can also be any suitable valve known to those skilled in the art such as a standard ball-cock valve or stop-cock valve 95.

The branch 84 further includes a micro-filter assembly 94 which is disposed in-line and in fluid communication with the branch 84. The filter assembly 94 allows for the aseptic introduction of drugs into the cerebrospinal fluid of a patient without the potential for delivery of harmful microorganisms into the cerebrospinal fluid. Preferably, the filter assembly 94 includes a membrane-type or micro-pore filter 96 disposed substantially perpendicular with respect to the lumen 82 and fluid flow path. That is, the filter 96 lies transversely across the lumen 82. The filter 96 can also include a support 98 which provides support to the filter 96 during the delivery of the drug therethrough to enable the filter 96 to withstand pressures applied by the fluid delivery device.

Figure 5:
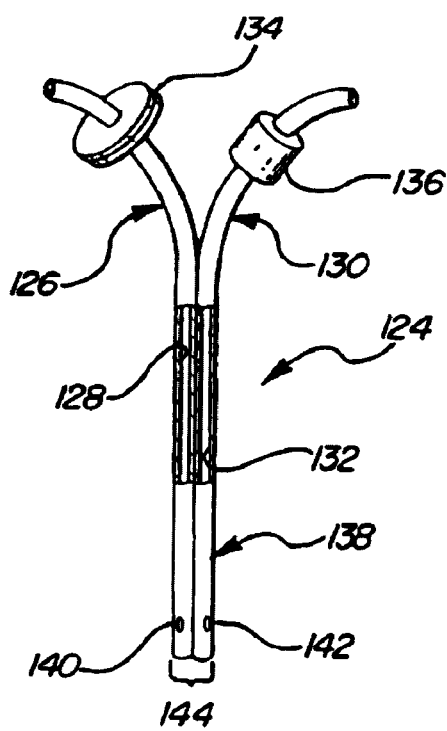
FIG. 5 is a schematic diagram illustrating an alternative embodiment of the CNS catheter of the present invention.

Referring to FIG. 5, a further alternative embodiment of the catheter assembly of the present invention is generally shown at 124. The catheter assembly 124 includes a first branch 126 which defines a first fluid lumen 128 therethrough and a second branch 130 which defines a second fluid lumen 60 therethrough. As already described above for the embodiment shown in FIG. 3, the first branch 126 is designed for the delivery of drugs into the CSF and includes a fluid filtering assembly 134. The second branch 130 which is designed for the monitoring of ICP and/or removal of CSF also includes a valve assembly 136 as described above.

In this embodiment, the first branch 126 and the second branch 130 each define their own lumen 128, 132, respectively. The catheter assembly 124 has the same "Y" shape as the embodiment illustrated in FIG. 3; however, the first 126 and second 130 branches come together to define a main body 138 but maintain separate and distinct fluid carrying lumens 128, 132. The lumen 128 includes at least one port 140 disposed therein for allowing the introduction or delivery of a drug into the CSF. The lumen 132 includes at least one port 142 which allows for the monitoring and/or removal of CSF from a patient. As described for the embodiment shown in FIG. 3, the catheter assembly 124 includes a proximally disposed end 144 wherein ends of each lumen 128, 132 may be open or closed, respectively, depending on design choice.

Figure 6:
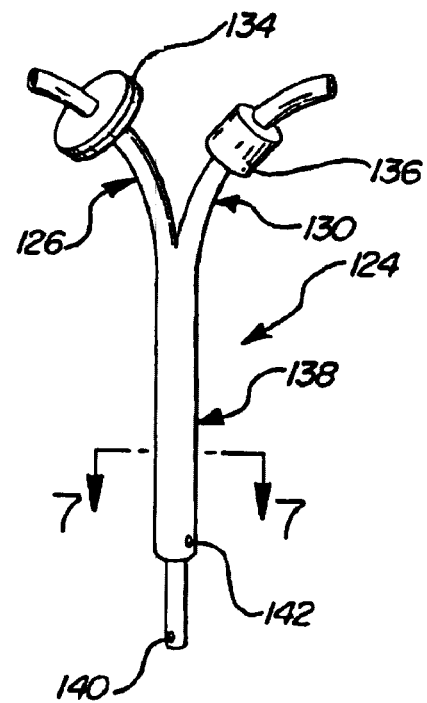
FIG. 6 is a schematic diagram illustrating a further alternative embodiment of the CNS catheter of the present invention.
Figure 7:
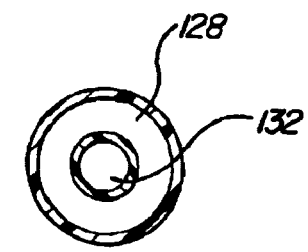
FIG. 7 is a cross-sectional view of a portion of the CNS catheter of the present invention taken along line 7—7 of FIG. 6.

Referring now to FIG. 6, a further alternative embodiment is illustrated wherein like numerals indicate like or corresponding parts throughout the several views. In this embodiment, rather than having the lumens 128, 132 of branches 126, 130 diverge into their separate respective lumens 128, 132 disposed adjacent to one another, the lumens 128, 132 are concentrically disposed with respect to one another as best shown in FIG. 7. That is, the first branch 126 and the second branch 130 remain separated from one another at the proximal end of the catheter assembly 124 while in the main body portion 138 of the catheter assembly 124, the branches 126, 130 and their respective lumens 128, 132 become concentrically disposed with respect to one another. As was the case for the embodiment illustrated in FIG. 5, each lumen 128, 132 can include at least one port 140, 142, respectively.

The branches 22, 24, 26, 84, 86, 126, 130 of the catheter assemblies 20, 80, 124 can be manufactured of any suitable material. Preferably the branches 22, 24, 26, 84, 86, 126, 130 are constructed of a plastic material such as silicone plastic.

The main body 28, 88, 138 is preferably made of a plastic material such as a silicone rubber compound for use as an intraventricular catheter and silicone plastic for use as an intrathecally.

All of the connectors or adapters are preferably industry norm standard connectors such as mating-type connectors or adapters, such as the Luer-lock type, or threaded connectors or adapters which reduce the likelihood that the connectors made therewith will inadvertently come apart potentially exposing the closed system to contamination.

Figure 8:
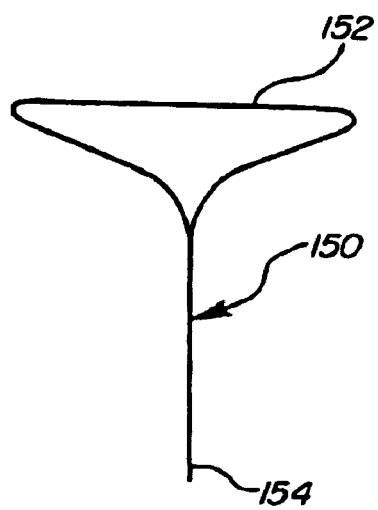
FIG. 8 is a front view of an insertion device for use with the present invention.
Figure 9:
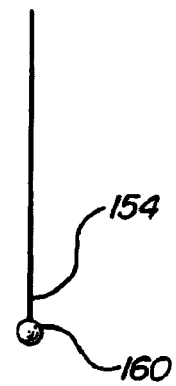
FIG. 9 is an enlarged view of an embodiment of the insertion apparatus.
Figure 10:
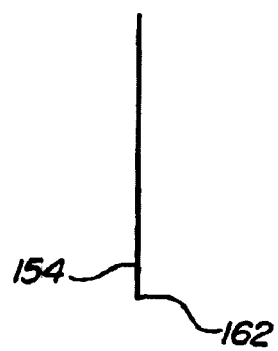
FIG. 10 is an alternative embodiment of the insertion apparatus.

Referring to FIGS. 8, 9 and 10, several embodiments of the wire insertion device are shown. FIGS. 8 and 10 show an insertion device 150 having a triangularly-shaped handle portion 152. The insertion device 150 includes a distal end 154 which is initially inserted into the lumen of the catheter assembly. As shown in FIG. 9, a ball 160 can be disposed as the distal end 154 of the insertion device 150. The ball 160 is of a specific size and shape such that it allows for the insertion of the insertion device 150 into the lumen of the catheter assembly without piercing the end 74, 144 of the main body 28, 88, 138 disposed in the patient.

Referring to FIG. 10, an alternative distal end configuration for the wire insertion device 150 is shown which includes a sharp point or cutting surface 162 disposed at its distal end 154 which is capable of piercing a closed end 74, 144 or diaphragm of the main body 28, 88, 138 upon insertion and proper placement of the assembly 20, 80, 124.

Figure 12:
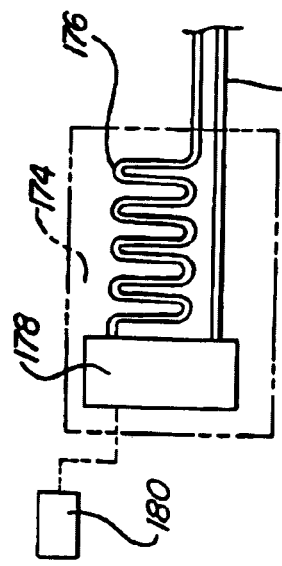
FIG. 12 is a schematic of a heat exchanger system operative in the present invention.
Figure 11:
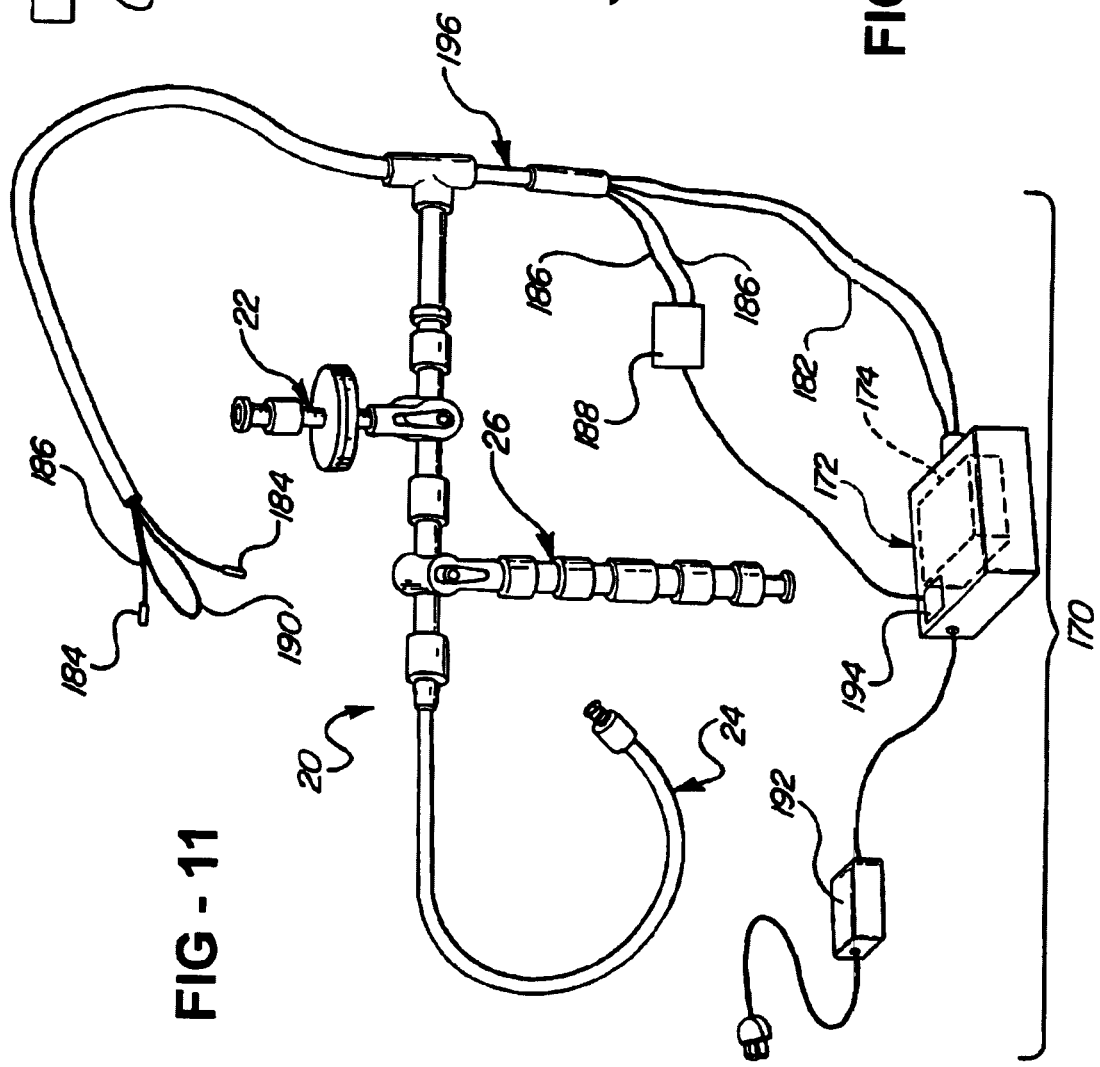
FIG. 11 is a schematic illustration of the temperature control system of the present invention coupled with a catheter of the present invention.

Referring to FIG. 11, a further embodiment of the present invention is shown. A temperature control system is generally shown at 170. The system 170 includes a temperature control mechanism 172 operatively connected to a direct central nervous system catheter 20 which is similar to the catheter assembly described above and as described hereinbelow. The temperature control mechanism 172 includes a reservoir 174 disposed therein for receiving and retaining a temperature conducting fluid or thermal transfer fluid such as ethylene glycol, water or normal saline or other suitable materials such as polyethylene glycol therein. Referring to FIG. 12, a heat exchanger 176 is disposed within the reservoir 174 in contact with the thermal transfer fluid disposed in the reservoir 174. A pump 178 operatively connected to a pump controller 180 serves to move the thermal transfer fluid through the heat exchanger 176. A thermostatically controlled heating/cooling mechanism, disposed within the reservoir 174 selectively heats or cools the thermal transfer fluid disposed in contact therewith. The thermal transfer fluid contacts the heat exchanger 176 and thereby regulates the temperature of the thermal transfer fluid being circulated or pumped to the CNS location. A conduit 182 is connected in fluid communication with the heat exchanger 174 to form a closed loop system. The conduit 182 is connected in fluid communication with the heat exchanger 174 and serves to transport the thermal transfer fluid from the heat exchanger 174 into the central nervous system of a subject in order to directly control the local temperature of the central nervous system of the subject through contact with either the CSF or CNS tissue itself.

The temperature control system 170 can also include a temperature sensor or element 184 which is connected in electrical communication via line 186 to a temperature computation device 188 which is connected to the control mechanism 172. The temperature sensor or element 184 can be a thermistor or similar device which converts temperature measurement into an electrical signal which is converted to a temperature readout by the temperature computation device 188. The temperature sensor or element 184 is disposed in contact with or directly adjacent to the central nervous system fluid (CSF) or tissue of the subject in general proximity to or adjacent to a closed end 190 of the conduit 182 in order to ascertain temperature measurements of the central nervous system in the general vicinity of the closed end 190 of the conduit 182.

The temperature control mechanism 172 can be powered by a power supply 194 which provides a predefined source of current to the temperature control device 172 in order for its operation.

The temperature control mechanism 172 can also include a controller or central processing unit (CPU) 194 which provides overall control to the temperature maintenance and to the operation of the temperature control mechanism 172. Additionally, a pump controller 180 can be connected in electrical communication with the pump 178 to further aid in the control of the rate of flow and the temperature management of the thermal transfer fluid.

Referring again specifically to FIG. 11, the temperature control system 170 preferably is combined with a direct central nervous system catheter assembly 20, 88, 124, as described in detail above, which includes a first branch 22, 84, 126, a second branch 24, 86, 130, or an optional third branch 26 operatively connected to a main body 28, 88, 138 which defines at least one lumen therein.

Unique to the embodiment shown in FIG. 11, the catheter assembly 20 includes a fourth branch 196 in which the closed loop end 190 of the temperature control device 172 is inserted in order to be placed within or adjacent to the central nervous system and/or central nervous system fluid (i.e. CSF). The temperature sensor or element 184 can also be inserted through the branch 196 in order to be placed in contact with the central nervous system and/or adjacent to the closed end 190 of the conduit 182 of the temperature control mechanism 172.

In operation, the direct central nervous system catheter assembly 20 would be disposed within either the intraventricular space or the spinal canal of a subject in order to place the end 74, 144 of the portion of the catheter body inserted into the patient either in contact with or adjacent to the cerebrospinal fluid. The closed loop end 190 of the conduit 182 would be disposed within the lumen defined by the branch into which the closed end 190 is inserted and would be moved through the main body 28, 88, 138 of the catheter assembly 20, 80, 124 into contact with the cerebrospinal fluid. The temperature sensor or element 184 could also be placed within the intraventricular space or spinal canal concurrently with the placement of the closed end 190 of the conduit 182 or optionally could be placed either before or after the placement of the closed end 190 of the conduit 182. Following proper positioning of the closed end 190 of the conduit 182, thermal transfer fluid having a desired temperature can be pumped through the conduit 182 where it would flow to the closed end 190 and via the heat transfer capacity of the conduit material and/or thermal transfer fluid, either heat or cool the central nervous system fluid. The thermal transfer fluid would then return to the temperature control device 172 via the conduit 182 where it would be recycled through the heat exchanger 176 and recirculated back to the closed end 190 of the conduit 182 for further control of the temperature at the desired CNS site. The flow rate and temperature of the thermal transfer fluid can be adjusted to regulate the temperature.

The conduit 182 is preferably made of a material which has suitable heat transfer characteristics embodied by various types of plastic tubing.

The catheter assembly 20, 80, 124 of the present invention provides a system that allows for the monitoring of ICP, sampling of CSF, drug delivery, and/or temperature regulation of the CSF of a patient or subject without opening the catheter system to the environment after the catheter assembly has been placed. That is, once the catheter assembly of the present invention is inserted into a patient, all of the immediately recited functions can be accomplished by connecting the appropriate device to the appropriate branch and manipulating the proper valves accordingly. Thus, all of the functions can be accomplished aseptically without directly exposing the CNS to the external atmosphere where pathogens could be present.

Figure 13:
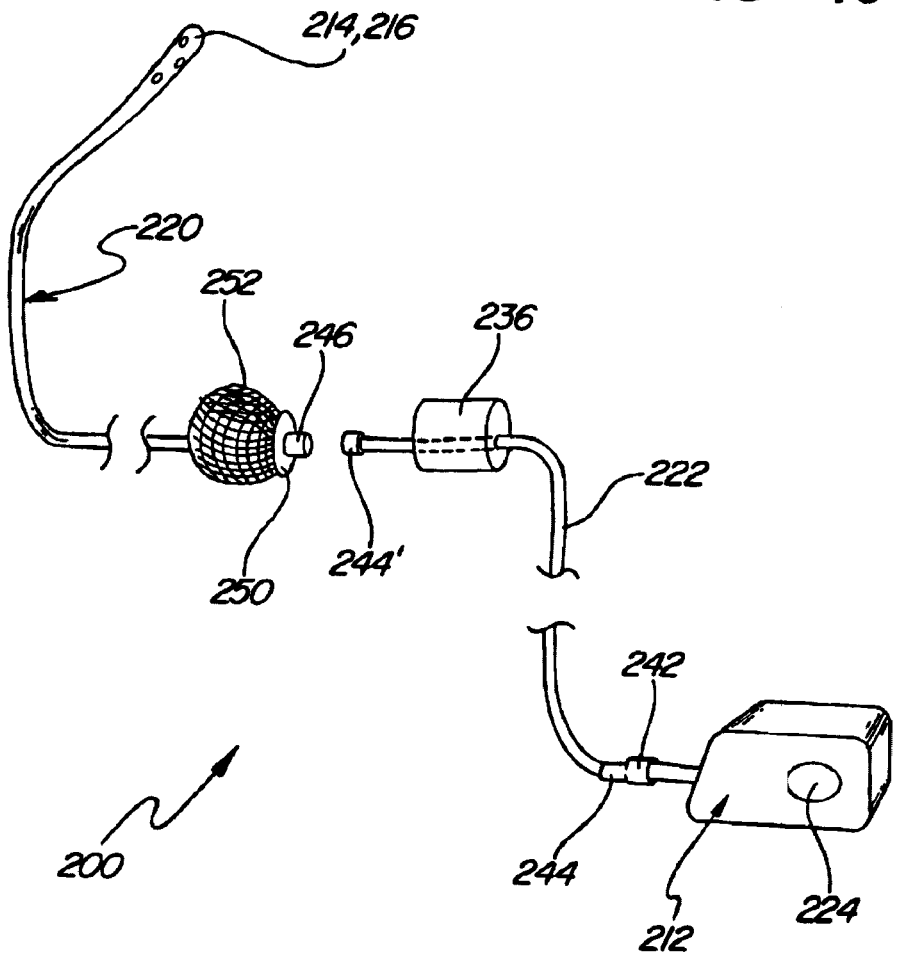
FIG. 13 is a schematic diagram illustrating a further alternative embodiment of the CNS catheter of the present invention.

Referring now to FIG. 13, a further alternative embodiment is illustrated of the central nervous system (CNS) catheter assembly generally at 200. The assembly 200 has an external pump 212 that permits the delivery of a variety of drugs and vectors in a sterile manner to the intraventricular end 214 or, alternatively, the intrathecal end 216 of a catheter 220 are connected to a replaceable intermediate catheter branch 222. The external pump 212 is a disposable low cost pump. Preferably, the pump 212 is battery powered and more preferably has a refillable pump chamber 224. The pump 212 is connected to the intermediate branch catheter 222 by a valve 242. The valve 242 is preferably a one-way valve or other suitable type or design including a ball valve, or one-way needle insertion valve, or any other type or design known to those skilled in the art which remains in a closed position to drug delivery until the pressure exerted on the valve by the drug delivery forces the valve to an open position. A complementary one-way valve fitting 244 connects the valve 242 of pump 212. Preferably, the complementary one-way valve fitting 244 is a male needle head one-way valve. The branch 222 further includes a microfilter assembly 236 which is disposed in line and in fluid communication with the branch 222. The filter assembly 236 allows for the aseptic introduction of drugs or vectors through the assembly 200 without the potential for delivery of harmful microorganisms therewith. The microfilter assembly 236 corresponds to the microfilter assembly 36 described with respect to FIG. 1. Branch 222 terminates in a one-way valve head 244' similar to one-way valve fitting 244. Preferably, the one-way valve fitting 244' is a male needle head one-way valve. One-way valve fitting 244' is adapted to engage a complementary valve 246 of the catheter 220. Preferably, the one-way valve 246 is a one-way needle insertion valve similar to that detailed with respect to valve 242. As catheter 220 is implanted, the one-way valve 246 is backed by a coverlet 250 serving as a physical barrier to infection and thereby permitting repeated antibiotic applications. Preferably, the coverlet 250 is adhered to the dermal layer about the catheter 220 with a surgical adhesive. Preferably, to facilitate structural adherence of the replaceable intermediate catheter within the patient body, a mesh 252 surrounds the portion of the catheter 220 that traverses the dermal layer. The mesh 252 is attached to the catheter tube 220 and the coverlet 250. The mesh 252 serves to allow skin to interpenetrate the mesh 252 and thereby stabilize the implanted catheter assembly. The mesh 252 is formed of any surgically implantable mesh material conventional to the art illustratively including stainless steel, titanium, fluoropolymer, polyamides and biologically surface modified forms thereof. The catheter 220 is in fluid communication with an intraventricular end 214 or intrathecal end 216 of the catheter according to the present invention. Thus, the external pump catheter assembly 200 according to the present invention is able to deliver a variety of drugs and vectors for times extending up to and beyond six months in a sterile and controlled manner. The external pump 212 is readily disconnected temporarily for service or aseptic refilling of the pump chamber 224.

Figure 14:
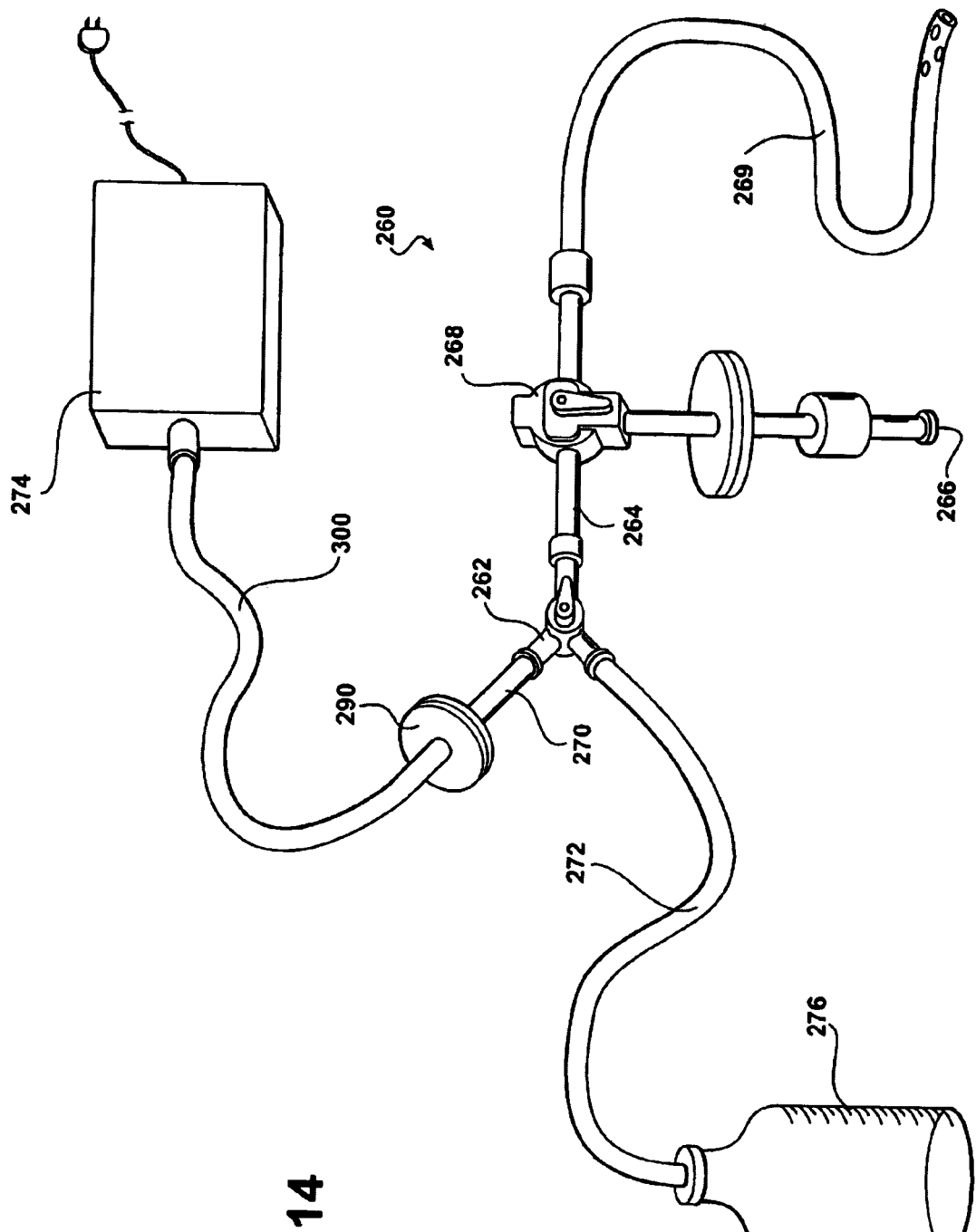
FIG. 14 is a schematic diagram illustrating a further alternative embodiment of the CNS catheter of the present invention.

Referring to FIG. 14, an embodiment of a catheter assembly 260 according to the present invention includes a position control valve 262 disposed distally to the main catheter body lumen 264 relative to the patient. The valve 262 is in fluid communication with the catheter insertion lumen 269 and a drug delivery port 266 via a main catheter body lumen 264 and an optional position control valve 268. The position control valve 262 is positionable to regulate flow between the main catheter body lumen 264, a first branch lumen 270 and an optional second branch lumen 272. In a preferred embodiment, the first branch lumen 270 is in communication with an ICP/osmotic pressure monitoring system 274. In a further preferred embodiment, an inventive catheter assembly includes a fluid drainage system 276 in fluid communication with the second branch lumen 272. In this configuration, valve 262 may be opened to independently provide for drainage of CSF and intracranial pressure measurement. Valve 262 may also be configured to allow simultaneous drainage and pressure measurement. Alternatively, the fluid drainage system 276 is in fluid communication with another branch of the catheter assembly, such as the main catheter body lumen 264 or the first branch lumen 270.

As noted, an intracranial pressure or osmotic pressure (ICP/OP) measuring and monitoring subsystem 274 is preferably included in the catheter assembly 260. ICP may be measured by including a pressure sensor transducer in communication with the main catheter body lumen 264 when valve 262 is open. A pressure sensor transducer included in subsystem 274 is any of various types that are known in the art and commercially available.

Optionally, the ICP/OP subsystem 274 includes a sterile field maintenance shield 290. An advantage of including a shield is that it allows repeated hook-up and disconnect of ICP/OP monitoring devices to permit such activities as patient movement, CSF drainage and therapeutic agent delivery without loss of closed field. A shield 290 is not permeable and thus prevents contamination of the patient through the catheter assembly. The shield typically includes a frame having an adaptor so that conduit tubing can be attached. The frame holds a sterile, impermeable material, illustratively including a plastic film such as polyvinylidene. One side of the shield is in fluid communication with a catheter branch lumen 270, while the opposite side is in contact with a conduction medium present in a catheter branch lumen 300. The conduction medium is preferably liquid, but may also be a gas, gel or solid, as long as ICP/OP changes are transmitted through the shield and carried via the conduction medium to a pressure sensor transducer included in subsystem 274. Alternatively, a pressure sensor may be configured to directly sense changes at the shield.

A drainage subsystem 276 is optionally included in the catheter assembly 260 for removal of patient fluid. Included in a drainage subsystem 276 is a CSF collection chamber. The collection chamber is illustratively a disposable container, such as a syringe or plastic bottle, attachable to a branch conduit 272. The collection chamber is optionally used as a specimen collection device, such that following drainage into the container, the container is detached from the catheter assembly for testing or storage. In use, the drainage subsystem is operable when valve 262 is opened to permit fluid flow into branch conduit 272. ICP/OP monitoring may be performed concurrently with a fluid removal procedure by appropriate positioning of valve 262.

Figures 1, 15A:
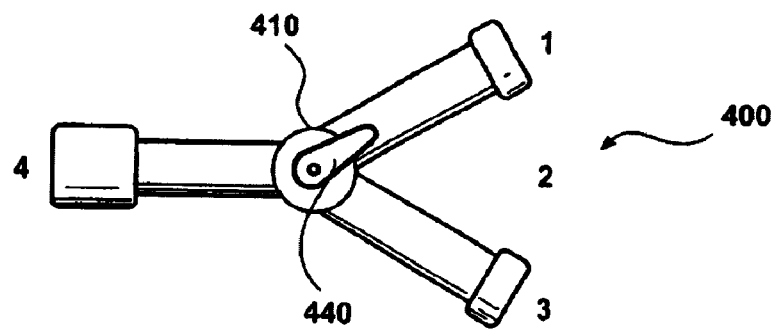
FIG. 15A is a schematic diagram illustrating a valve optionally included in a CNS catheter of the present invention.
Figures 2, 15A:
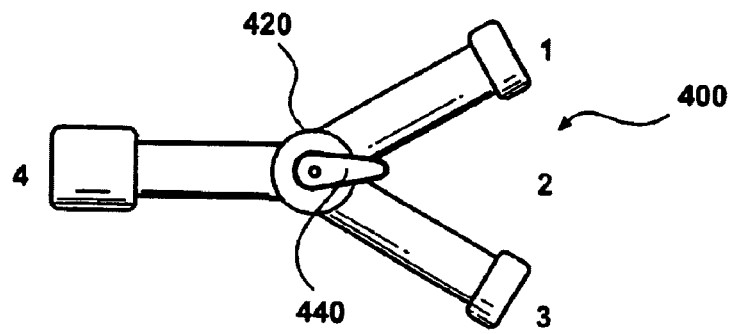
Figures 3, 15A:
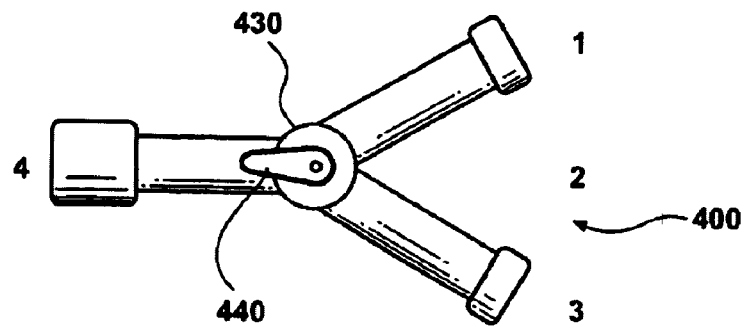

Preferably, valve 262 is a 4-position Y-valve as exemplified in FIG. 15A at 400. A 4-position Y-valve closes fluid communication between a first branch conduit (1) and a main conduit (4) in a first position 410; a second branch conduit (3) and the main conduit (4) in a second position (not shown); in a third position 420, a first branch lumen (1), a second branch conduit (2) and the main conduit (4) are in fluid communication; and in a fourth position 430, communication between both branches (1 and 2) and the main conduit (4) is closed. A change in the position of a flow regulation handle (440) results in a deviation of the path of fluid flow between the branch and main conduits as described and illustrated. It has been found that a 20–40 degree angle, and preferably a 30 degree angle, between the first and second branch conduits is optimal. This arrangement allows for smooth passage of fluid from the main conduit to either the first branch, second branch or both. Optionally, a flow regulation handle contains a directional display (450) to indicate which of the possible pathways through the valve are currently open or closed. For example, a handle with directional display, as shown in FIG. 14A indicates that a conduit is closed when the handle is manipulated to be in a position parallel to the direction of flow through that conduit.

Figure 15B:
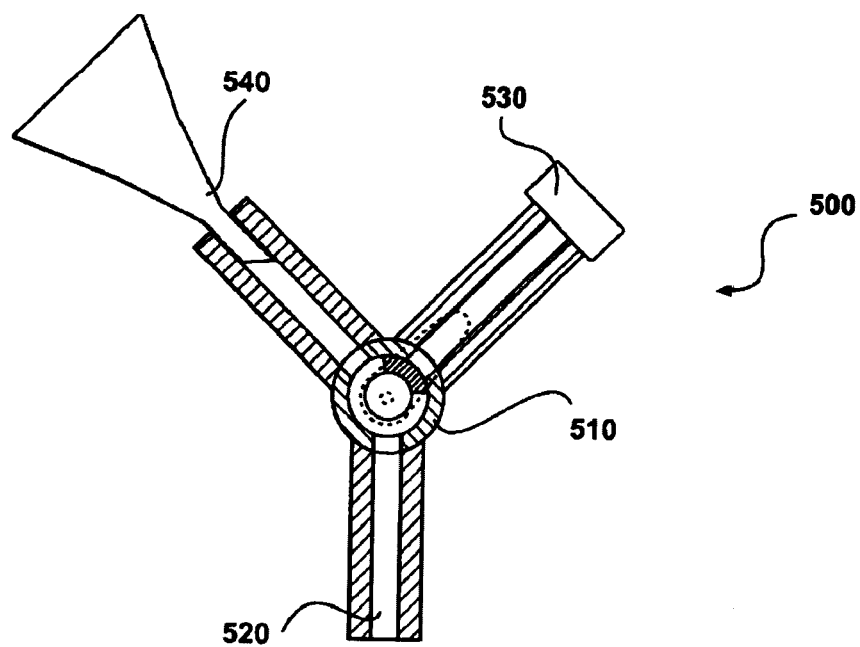
FIG. 15B is a schematic diagram illustrating a valve optionally included in a CNS catheter of the present invention.

In some embodiments of a catheter assembly, communication between a first and second branch conduit is undesirable. In such cases a "swing positioning" Y-valve (500) as illustrated in FIG. 15B is included in a catheter assembly. A swing positioning Y-valve "swings" upon operation of a rotating handle or toggle switch (510) and then locks into 1 of 2 possible desired positions. A first position allows exclusive communication between a main conduit (520) and a first branch conduit (530), while a second position provides exclusive communication between a main conduit (520) and a second branch conduit (540).

Figure 16A:
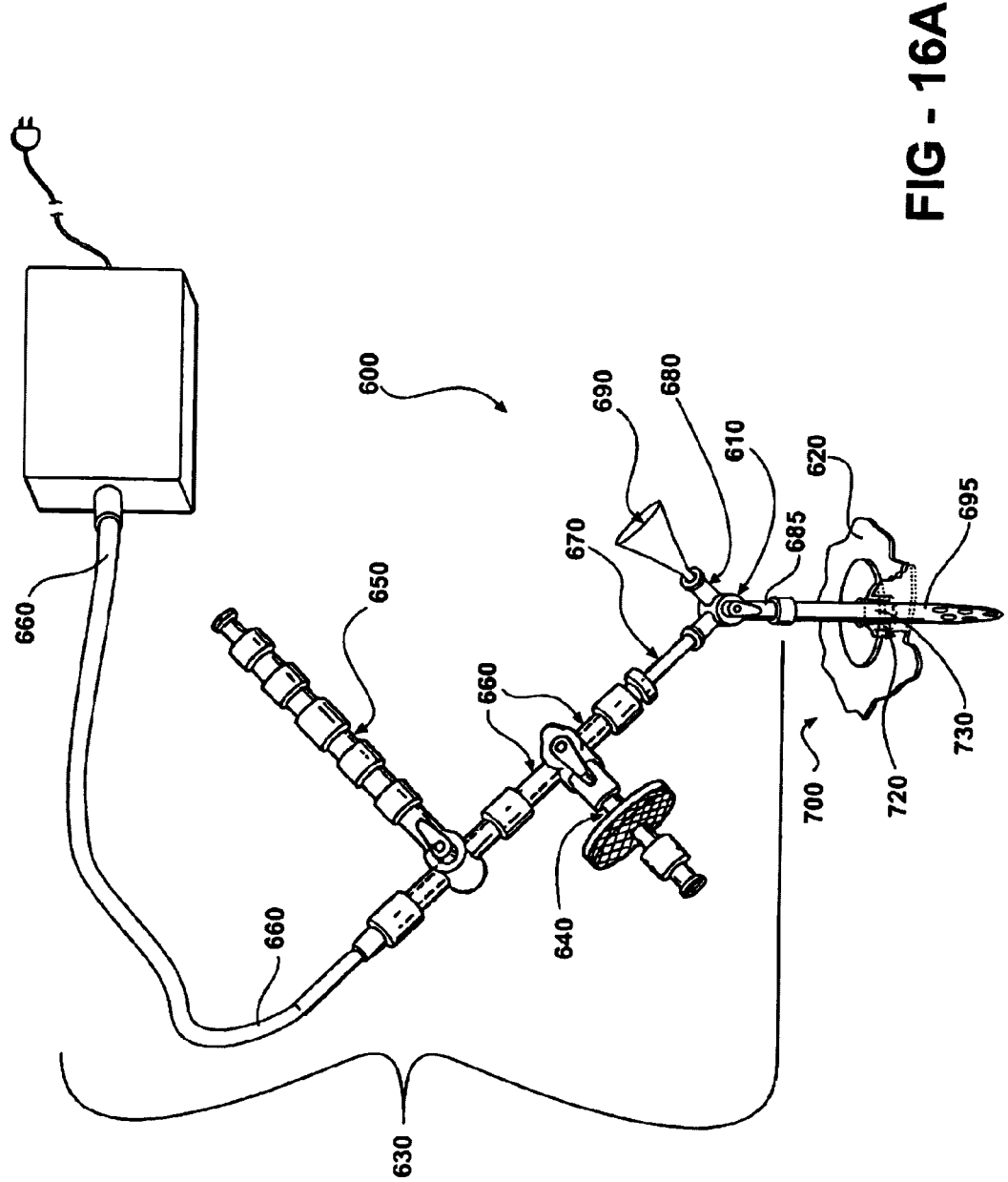
FIG. 16A is a schematic diagram illustrating a further alternative embodiment of the CNS catheter of the present invention.
Figure 16B:
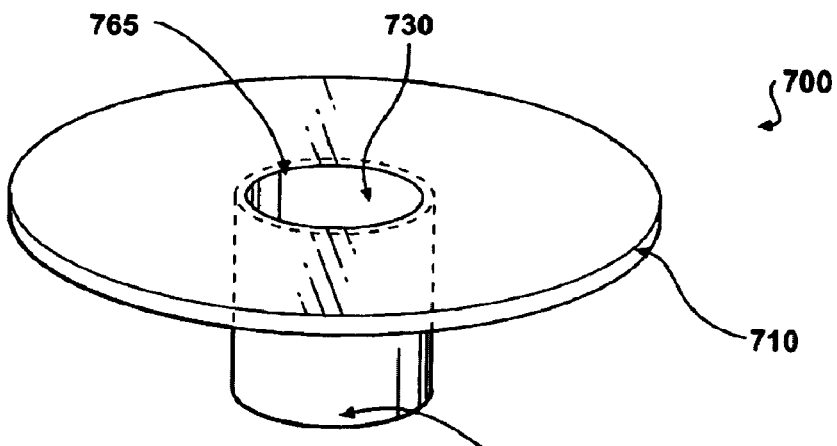
FIG. 16B is a perspective view illustrating a patient surface attachment aid optionally included in a CNS catheter of the present invention.
Figure 16C:
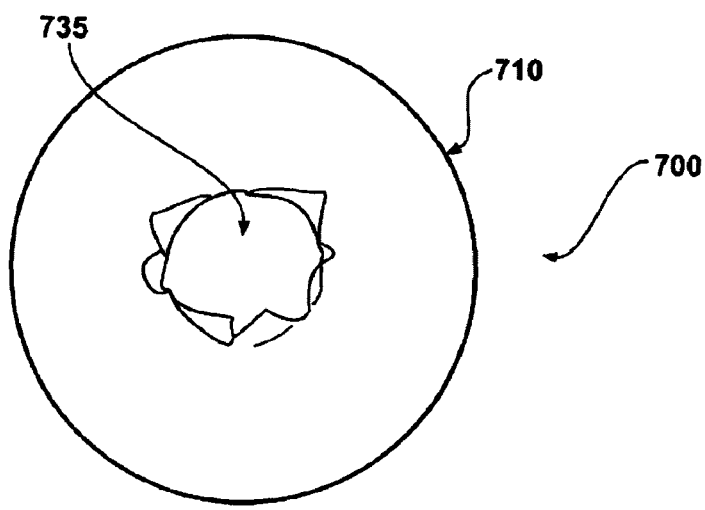
FIG. 16C is a bottom view of the patient surface attachment aid of FIG. 16B having a small diameter.
Figure 16D:
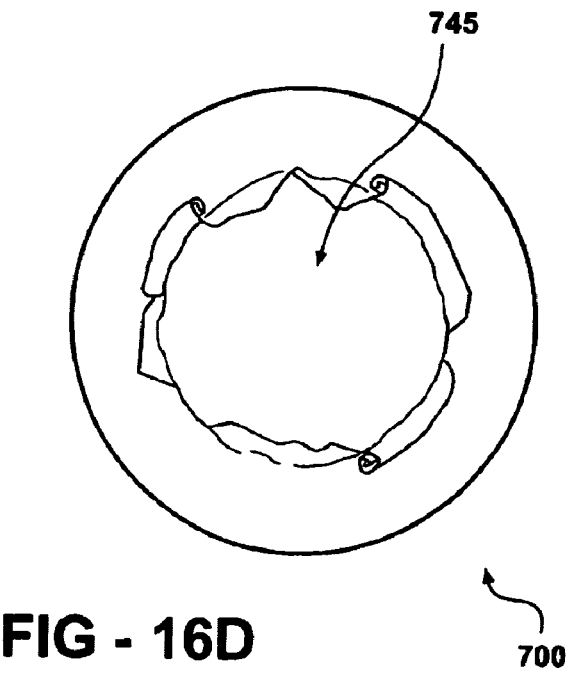
FIG. 16D is a schematic diagram illustrating a patient surface attachment aid optionally included in a CNS catheter of the present invention.

A swing position Y-valve or the like is particularly preferred in a catheter assembly 600 illustrated in FIG. 16A. FIG. 16A illustrates a catheter assembly in which a Y-valve 610 is included proximal to the skull of a patient 620 relative to the main valve assembly 630. The main valve assembly 630 includes components previously described such as a first branch lumen 640, a second branch lumen 650 and a main catheter body lumen 660. A first branch conduit 670 of the Y-valve is in fluid communication with the main valve assembly 630. A second branch conduit 680 of the Y-valve is available as a port for insertion of tubing, wires or other apparatus into a brain ventricle, intrathecal space or other brain or spinal cord region of interest in the patient. The main conduit 685 of the Y-valve 610 is in communication with insertable catheter portion 695 which is inserted into the patient's brain or spinal column. A valve having a device insertion port is optionally specially adapted for device introduction by internal smoothing. As a further option, an attachable introduction aid 690 may be used for guiding elements into the valve 610. It is recognized that a Y-valve or swing valve may be used as desired in any embodiment of an inventive catheter.

A catheter assembly of the present invention optionally includes a patient surface attachment aid shown at 700 in FIGS. 16A–D. The attachment aid 700 provides protection to the patient and to delicate catheter components as they are inserted through the opening in the skull. The attachment aid 700 is typically made of a sterilizable flexible material such as silicon. As shown in FIGS. 16A–D, an attachment aid 700 includes an attachment surface 710 contacting an outer aspect of a patient's body, for instance the patient's skull 620 where a ventriculostomy is performed. The attachment surface 710 ranges in thickness from about 1–5 millimeters. The attachment aid 700 includes an extension 720 having an opening 730 that may be sized to fit snugly just inside a standard ventriculostomy opening to allow insertion of a catheter. The extension opening 730 may be preformed to a specific size. For example, for use in a typical skull drill hole, which is between 6–7 millimeters in diameter, a surface attachment extension opening 730 of similar size is chosen. Alternatively, a surface attachment extension opening 730 may be configured to expand from a smaller diameter 735 to a larger diameter 745 inside the ventriculostomy opening to ensure a tight fit against the skull wall 760. An optional locking system (not shown) may be engaged to ensure that the expanded extension maintains the desired opening size. For example, surface attachment extension opening 730 diameter may range from 3–5 mm expandable to 6–10 mm. The surface attachment extension 720 typically ranges from 1–10 mm in height, from the aspect of the extension proximal to the patient's brain or spinal cord and 1–5 mm in thickness.

Figure 17:
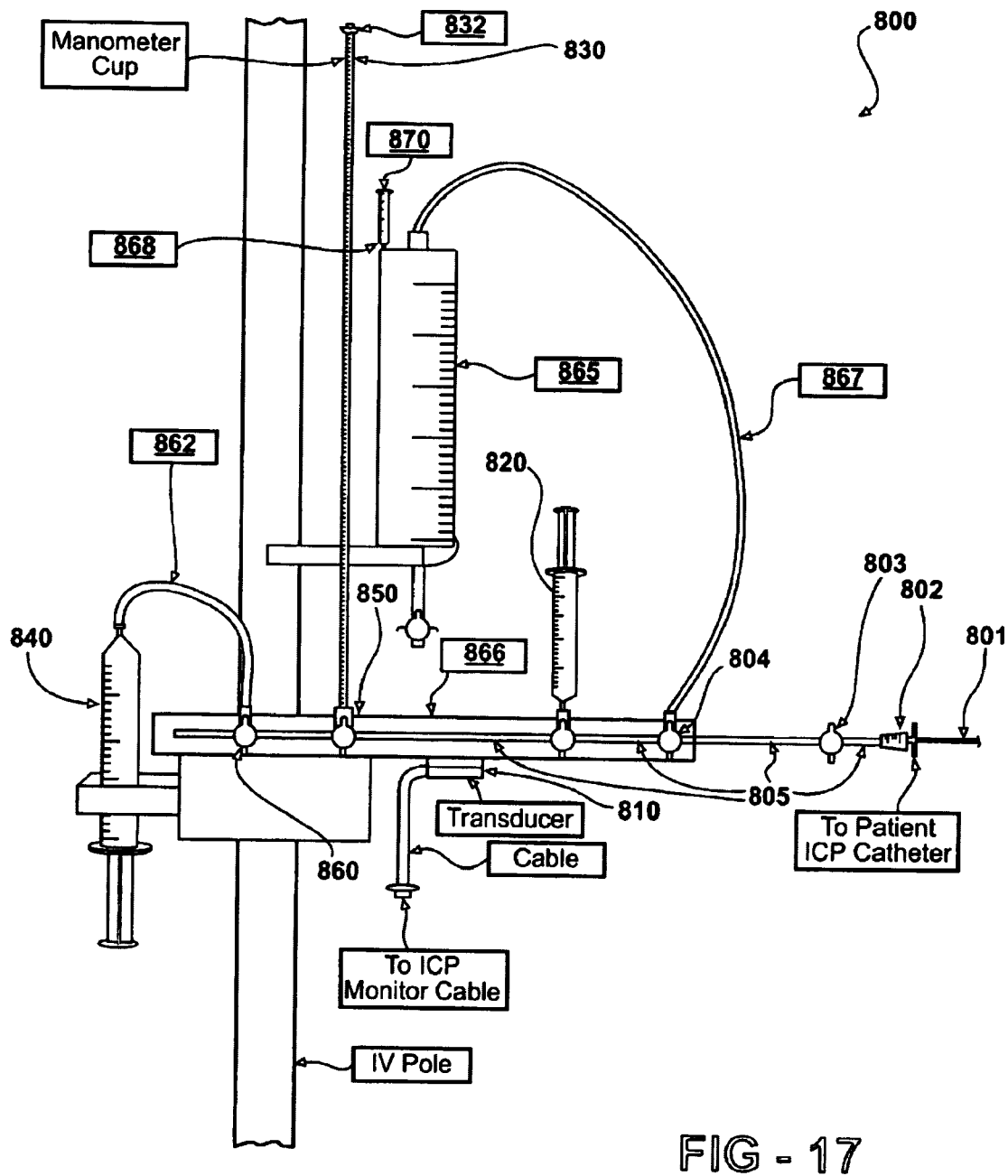
FIG. 17 is a schematic diagram illustrating an intracranial pressure evaluation and relief system optionally included in a CNS catheter of the present invention.

FIG. 17 depicts an alternative embodiment of a catheter assembly according to the present invention having an intracranial pressure monitoring system and drainage system controlled by separate valves. In this configuration, a conduit 801 connected to the main valve assembly, such as those shown at 20, 80, 124 and 630 of FIGS. 1, 3, 5 and 16A, respectively, is included in a comprehensive intracranial pressure evaluation and relief system (CIPER) (800). The CIPER system 800 is isolated from the main valve assembly by an optional filter 802 which prevents contamination of the main valve assembly and of the patient. The CIPER system is further isolated from the main valve assembly by a positional direction valve 803. The CIPER system 800 further includes an optional positional direction valve 804 which diverts patient fluid from the main lumen 805 in communication with conduit 801 into a CSF collection chamber when the valve 804 is open. The CIPER system further includes a pressure transducer 810 for measuring intracranial or intrathecal pressure. Various optional components are included in the CIPER system including an irrigation pump or syringe 820, a manometer 830 and a fluid reservoir pump or syringe 840. Each of these components may be controlled by opening a valve connected to the conduit 850.

Filters are optional components of an inventive catheter assembly that may be included in various configurations. Filters are particularly important at points in the catheter assembly where exogenous substances are introduced, such as drug delivery ports. A filter may also be desirable near device ports where contamination may be introduced during connection/disconnection of various system components, such as a sample collection chamber or ICP monitor. For example, see filters illustrated in FIG. 1 at 38 and FIG. 16A at 802. Anti-contamination filters useful in an inventive catheter assembly include those known in the art such as 0.1 or 0.22 micron PVDF or cellulose ester filters. In order to reduce the possibility of contamination by very small particles such as mycoplasma, virus or prions, a PEM (proton enabled membrane or proton exchange membrane) filter is optionally included in a catheter assembly of the present invention. A proton exchange membrane filter includes a polymer electrolyte such as NAFION™. The PEM may be mounted in a filter housing equipped with adaptors for attachment to tubing, valves or others catheter assembly components.

It will be apparent to one of skill in the art that components of the catheter assembly such as valves, filters, tubing and apparatus may be attached by adapters, including male and female Luer connectors or other such adapters known in the art. Further, materials and methods described as applicable for use with catheter assemblies described referring to FIGS. 1–13 are also applicable in catheters described referring to subsequent figures.

Figure 18A:
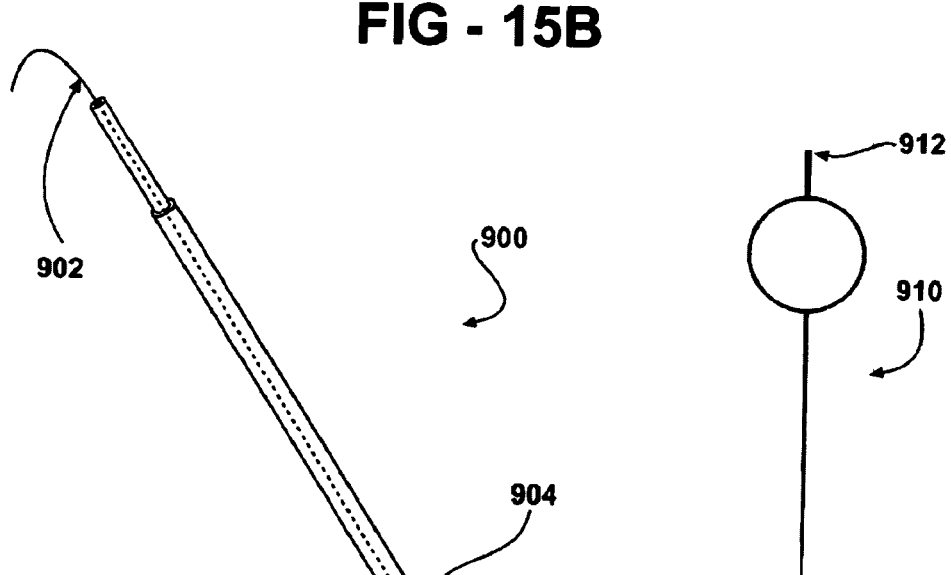
FIG. 18A is a schematic diagram illustrating a micromanipulator optionally included in a CNS catheter of the present invention.
Figure 18B:
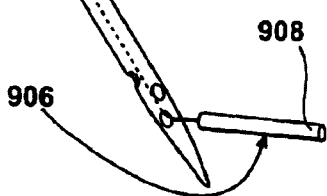
FIG. 18B is a schematic diagram illustrating a micromanipulator optionally included in a CNS catheter of the present invention.

In another embodiment of an inventive catheter assembly, an insertion system is included that allows introduction of a micromanipulator into the patient. A micromanipulator is illustratively used for accurate placement of a therapeutic agent, such as a stem cell, a genetically manipulated cell or a miniature osmotic pump containing a drug. Further, a micomanipulator is used to maneuver a microinstrument, such as a cutting tool or electrical stimulator, during a therapeutic procedure. A micromanipulator is controlled directly, such as by a skilled technician physically moving a control device attached to the micromanipulator, or indirectly, such as by remote control. An exemplary direct micromanipulator is illustrated in FIG. 18A which shows a wire micromanipulator system 902 threaded through a tube 904 which is inserted into the patient. The exemplary wire system includes two wires terminating at the distal end in a clip 906. The proximal ends are manipulated so that the clip end opens and closes thereby permitting the holding and placement of a therapeutic agent or microinstrument 908. An indirect micromanipulator illustratively includes a nano-robot 910 as shown in FIG. 18B. A micromanipulator is preferably inserted through a device insertion port included in an inventive catheter assembly, for example, that shown in FIG. 16A at 680.

The nano-robot is of mechanical or biological construction. The nano-robot is directed by an external source through methods conventional to the art, these external communication methods illustratively including radio frequency (RF) communication or connection to external controls by a fine wire providing outside control combined with internal response to external direction capabilities. It is appreciated that a nano-robot of the present invention is optionally self-directed to a predetermined objective. Methods of nano-robot self-directed navigation illustratively include electromagnetic positioning as detailed in U.S. Pat. No. 4,737,794 or following chemical or pressure gradients with a suitable on-board sensor. A mechanical nano-robot as used herein contains a battery, other source of power, or simply operates on physiological electric power; imaging; and control processing capabilities that illustratively include the ability to navigate to its objective and accomplish a therapeutic or analysis mission. A nano-robot mission includes delivery of, or sensing of, a biological or chemical agent or marker. A biological nano-robot is an organic molecular structure that illustratively is a modified virus, polypeptide, antibody, or enzymatic substrate that releases therapeutic or analysis molecule. A biological nano-robot is illustratively guided by amino-acid trails to the site objective or illustratively responds to a marker existing or pre-positioned in the objective.

In view of the teaching presented herein, other modifications and variations of the present inventions will be readily apparent to those of skill in the art. The foregoing drawings, discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. A central nervous system (CNS) catheter assembly adapted for use as a ventriculostomy catheter and a spinal catheter, said CNS catheter assembly comprising:
    a catheter body defining at least one lumen therethrough having at least a first branch and a second branch, said first branch and said second branch in fluid communication with said at least one lumen and having a fixed displacement therebetween, said catheter body having an insertable portion for insertion within a ventricle space or spinal canal of a subject;
    an opening in fluid communication with said at least one lumen disposed at a proximal end of said first branch;
    an opening in fluid communication with said at least one lumen disposed at a proximal end of said second branch;
    at least one opening in fluid communication with said at least one lumen disposed at a distal end of said catheter body;
    an aseptic drug delivery filter assembly disposed in fluid communication with said first branch;
    a first valve disposed in fluid communication with said second branch; and
    a component in fluid communication with said at least one lumen and having said first branch and said second branch intermediate between said component and the insertable portion of said catheter body or intersects said second branch at said first valve, said component selected from the group consisting of: an intracranial pressure/osmotic pressure monitoring system, and an intracranial pressure evaluation and relief system.

2. A catheter assembly according to claim 1, further comprising a second valve disposed in fluid communication with said first branch.

3. A catheter assembly according to claim 1, wherein said filter assembly comprises a micro-pore filter.

4. A catheter assembly according to claim 1, wherein said filter assembly comprises a membrane filter.

5. A catheter assembly according to claim 4, wherein said membrane filter is a positron emission membrane filter.

6. A catheter assembly according to claim 2, wherein said second valve is a one-way flow valve.

7. A catheter assembly according to claim 1, wherein said catheter body has a single lumen.

8. A catheter assembly according to claim 1, further comprising a first connector disposed at the proximal end of said first branch.

9. A catheter assembly according to claim 1, wherein said second branch comprises a second connector disposed at the proximal end thereof.

10. A catheter assembly according to claim 1 further comprising a third branch disposed in fluid communication with said catheter body.

11. A catheter assembly according to claim 10 further comprising a third valve disposed in fluid communication with said catheter body and said third branch.

12. A catheter assembly according to claim 1 wherein said first valve is a Y-valve.

13. A catheter assembly according to claim 1 wherein said first valve is a swing valve.

14. A method for aseptic drug delivery to the central nervous system through a catheter and cerebrospinal fluid, and monitoring of intracranial pressure or intraspinal pressure, said method comprising:
    inserting a catheter according to claim 1 into at least one of: a ventricular space and a spinal canal; and
    delivering a drug through the first branch by positioning the second valve in the first position without opening the catheter to the atmosphere.

15. A method according to claim 14 further comprising monitoring intracranial or intraspinal pressure by connecting a pressure monitoring device to the second branch.

16. A method according to claim 14 further comprising the removing cerebrospinal fluid through a third branch without opening the catheter to the atmosphere.

17. A method according to claim 14 wherein said drug is delivered from an external pump through the first branch.

18. A central nervous system (CNS) catheter assembly adapted for use as a ventriculostomy catheter and a spinal catheter, said CNS catheter assembly comprising:

a catheter body defining at least one lumen therethrough having at least a first branch and a second branch, said first branch and said second branch in fluid communication with said at least one lumen and having a fixed displacement therebetween, said catheter body having an insertable portion for insertion within a ventricle space or spinal canal of a subject;

an opening in fluid communication with said at least one lumen disposed at a proximal end of said first branch;

an opening in fluid communication with said at least one lumen disposed at a proximal end of said second branch;

at least one opening in fluid communication with said at least one lumen disposed at a distal end of said catheter body;

an aseptic drug delivery filter assembly disposed in fluid communication with said first branch;

a first valve disposed in fluid communication with said second branch; and a component in fluid communication with said at least one lumen, said component selected from the group consisting of: an attachable introduction aid, a patient surface attachment aid, and a micromanipulator.

19. A catheter assembly according to claim 18, further comprising a second valve disposed in fluid communication with said first branch.

20. A catheter assembly according to claim 18, wherein said filter assembly comprises a micro-pore filter.

21. A catheter assembly according to claim 20, wherein said filter assembly comprises a membrane filter.

22. A catheter assembly according to claim 21, wherein said membrane filter is a positron emission membrane filter.

23. A catheter assembly according to claim 19, wherein said second valve is a one-way flow valve.

24. A catheter assembly according to claim 18, wherein said catheter body has a single lumen.

25. A catheter assembly according to claim 18, further comprising a first connector disposed at the proximal end of said first branch.

26. A catheter assembly according to claim 18, wherein said second branch comprises a second connector disposed at the proximal end thereof.

27. A catheter assembly according to claim 18 further comprising a third branch disposed in fluid communication with said catheter body.

28. A catheter assembly according to claim 27 further comprising a third valve disposed in fluid communication with said catheter body and said third branch.

29. A catheter assembly according to claim 18 wherein said first valve is a Y-valve.

30. A catheter assembly according to claim 18 wherein said first valve is a swing valve.

* * * * *